United States Patent [19]

Frola et al.

[11] Patent Number: 5,247,826
[45] Date of Patent: Sep. 28, 1993

[54] GAS CONCENTRATION AND/OR FLOW SENSOR

[75] Inventors: Frank R. Frola, Trafford; Dennis Gibboney, Mt. Pleasant; Paul Bauer, Brentwood, all of Pa.

[73] Assignee: DeVilbiss Health Care, Inc., Somerset, Pa.

[21] Appl. No.: 975,616

[22] Filed: Nov. 12, 1992

[51] Int. Cl.⁵ ............................................. G01N 29/18
[52] U.S. Cl. ................................ 73/24.01; 73/861.28
[58] Field of Search ............ 73/24.01, 861.27, 861.28, 73/861.29

[56] References Cited

U.S. PATENT DOCUMENTS

| | | |
|---|---|---|
| 3,805,590 | 4/1974 | Ringwall et al. |
| 4,520,654 | 6/1985 | Terhune |
| 4,630,482 | 12/1986 | Traina ................................. 73/597 |
| 4,938,066 | 7/1990 | Dorr .................................... 73/597 |
| 5,060,506 | 10/1991 | Douglas ............................ 73/24.01 |
| 5,060,507 | 10/1991 | Urmson et al. ................... 73/24.01 |
| 5,060,514 | 10/1991 | Aylsworth ........................ 73/24.01 |

FOREIGN PATENT DOCUMENTS

| | | |
|---|---|---|
| 2833793 | 2/1980 | Fed. Rep. of Germany ... 73/861.29 |
| 2210977 | 6/1989 | United Kingdom .............. 73/24.01 |

OTHER PUBLICATIONS

Ultrasonic Oxygen Sensor, W. R. Dagle, Report Prepared for USAF School Of Aerospace Medicine, Dec., 1987.

Primary Examiner—Hezron E. Williams
Assistant Examiner—Joseph W. Roskos
Attorney, Agent, or Firm—MacMillan, Sobanski & Todd

[57] ABSTRACT

A gas concentration and/or bulk flow rate sensor suitable for measuring the oxygen concentration and the bulk flow rate of gas delivered to a patient for medical purposes. Two piezoelectric transducers mounted on a printed circuit board are interconnected by an elongated coiled tube. The gas is flowed around one of the transducers, through the tube and around the other transducer. Periodically, one of the transducers is energized with a single short duration pulse to transmit a sonic wave through the gas to the other transducer. The travel time for the sonic wave is measured. The two transducers are alternately used as transmitters and receivers so that the wave travel time is measured both with and against the gas flow direction. A thermistor is located in the center of the coiled tube for measuring the temperature of the gas. From the measured times, the measured temperature and stored formulas, a microprocessor calculates the oxygen concentration and/or the bulk flow rate for the gas. The sensor also may be used to measure other components of a gas mixture.

15 Claims, 2 Drawing Sheets

GAS CONCENTRATION AND/OR FLOW SENSOR

TECHNICAL FIELD

The invention relates to sensors and more particularly to a gas concentration and flow sensor suitable, for example, for indicating the flow rate and concentration of oxygen in gas delivered to a patient for medical purposes.

BACKGROUND ART

Various types of sensors have been designed for measuring properties of gas. For example, sensors have been designed for measuring the percentage of a particular component in a gas mixture. Air is primarily made up of nitrogen, oxygen and lesser amounts of carbon dioxide and argon. Oxygen concentrators have been used for removing nitrogen and carbon dioxide from a flow of air. An oxygen concentrator may be used, for example, for supplying an oxygen rich product gas for medical purposes, for aircraft emergency gas supplies or for commercial purposes such as a source of oxygen for welding. The product gas from an oxygen concentrator of the molecular sieve type may be up to 95.7% oxygen with the remainder 4.3% argon which is not removed by the concentrator. It is desirable to have a gas concentration sensor capable of indicating the percentage of oxygen in the product gas from an oxygen concentrator. Also, it is desirable to have a sensor capable of indicating the bulk flow rate for the product gas from an oxygen concentrator. For medical applications, it may be critical to maintain a specific flow rate of gas having a predetermined high oxygen concentration to a patient. Sensors may be used to monitor the delivered gas to assure that the patient's requirements are met.

In a December, 1987 report for the USAF School of Aerospace Medicine, W. R. Dagle described a sensor capable of measuring both oxygen concentration of a flowing gas and the bulk flow rate. The gas flow is passed through a cylindrical chamber in a sensor housing. Two piezoelectric transducers are mounted on diametrically opposite sides of the chamber and are aligned along an axis inclined to the axis of gas flow through the chamber. A thermistor also is mounted to measure the temperature of the gas flowing through the chamber. Periodically, one of the transducers is driven with an electrical signal to emit a burst of ultrasonic energy into the chamber. The time required for the resulting ultrasonic wave to travel through the gas from the transmitting transducer to the receiving transducer is measured. The travel time is affected by the length of the path between the transducers, by the composition of the gas, by the temperature of the gas by the flow rate of the gas. Since the travel time is affected by the gas flow, the two transducers are alternately operated as transmitters and receivers so that alternate ultrasonic wave travel times will be measured in the gas flow direction and against the gas flow direction. The average of the two measured ultrasonic wave travel times through the gas and temperature of the gas are used for calculating the percentage of oxygen in the gas and the difference between the two measured times and the measured temperature are used for calculating the bulk flow rate of the gas. However, difficulties have occurred in manufacturing sensors of this type on a commercial scale which have a consistent high accuracy and a low manufacturing cost. Manufacturing tolerances are quite critical to the accuracy of the sensor.

Douglas U.S. Pat. No. 5,060,506 shows similar apparatus for measuring the concentration of a gas constituent. However, in the Douglas apparatus a very short sensing chamber (1.5 inches, 3.81 cm) is combined with a low flow rate in the sensing chamber. Together, these prevent measuring bidirectionally to produce meaningfully different travel times from which to calculate bulk flow rate. The transmitting transducer is excited with a burst of ultrasonic waves to transmit an ultrasonic wave burst through the gas. Sufficient time must be maintained between successive bursts to prevent standing waves causing noise problems in the test chamber.

DISCLOSURE OF INVENTION

According to the present invention, an improved sonic sensor has been developed for measuring the concentration of oxygen or of another component in a flowing binary gas mixture. In obvious extension, a gas of n components, (n−2) of which are in fixed ratio, may likewise be measured. As an example, carbon dioxide concentration in mixtures of air and carbon dioxide may be measured in incubators. The bulk flow rate of the gas through the sensor is also measured. The sensor includes a sonic cell and related control circuitry including a microprocessor which calculates the gas concentration and the bulk flow rate from stored formulas and data obtained from the sonic cell. The sonic cell includes two piezoelectric transducers are mounted in spaced relationship on a printed circuit board. A manifold block is attached to the printed circuit board to form a separate enclosed chamber for each transducer. The chambers are connected by an elongated small diameter tube which may be coiled to reduce its spatial requirements. The tube provides a path for sound waves to travel between the transducers which is significantly longer than the spacing between the transducers. The gas under test is delivered to one of the chambers, flows around the transducer in the chamber, flows through the elongated tube to the other chamber and around the other transducer, and is withdrawn from the other chamber. A thermistor is positioned in the center of the tube with its two lead wires exiting out opposite ends of the tube for accurately measuring the temperature of the gas flowing through the tube.

Periodically, one of the transducers is excited, preferably with a single pulse. A resulting sonic wave emitted from such transducer travels through the tube and is received by the other transducer. The travel time for the sonic wave to travel the length of the tube is measured and is stored in a microprocessor. The transducers are alternately excited so that two successive time measurements represent the forward and reverse travel times for sonic waves relative to the gas flow direction. These time measurements, the length of the path between the sensors and the measured temperature are used to calculate the percentage of oxygen or of another component of the gas and/or to calculate the bulk flow rate through the sonic cell.

The design of the sonic cell provides a long travel path for sound waves traveling between the transducers and provides for an accurate gas temperature measurement. The long path through the tube increases the accuracy of the sensor and reduces affects of normal manufacturing tolerances so that individual sensor calibration is simplified. Further, by using a small diameter tube, the gas velocity through the tube is increased, thus providing a higher resolution of the bulk flow rate.

Accordingly, it is an object of the invention to provide an improved sensor of the type which measures the concentration of a component of a gas and/or measures the flow rate of the gas by periodically transmitting a sonic wave through the gas and measuring the travel time for the sonic wave over a known distance.

Other objects and advantages of the invention will become apparent from the following detailed description of the invention and the accompanying drawings.

BEST MODE FOR CARRYING OUT THE INVENTION

Figure 1:
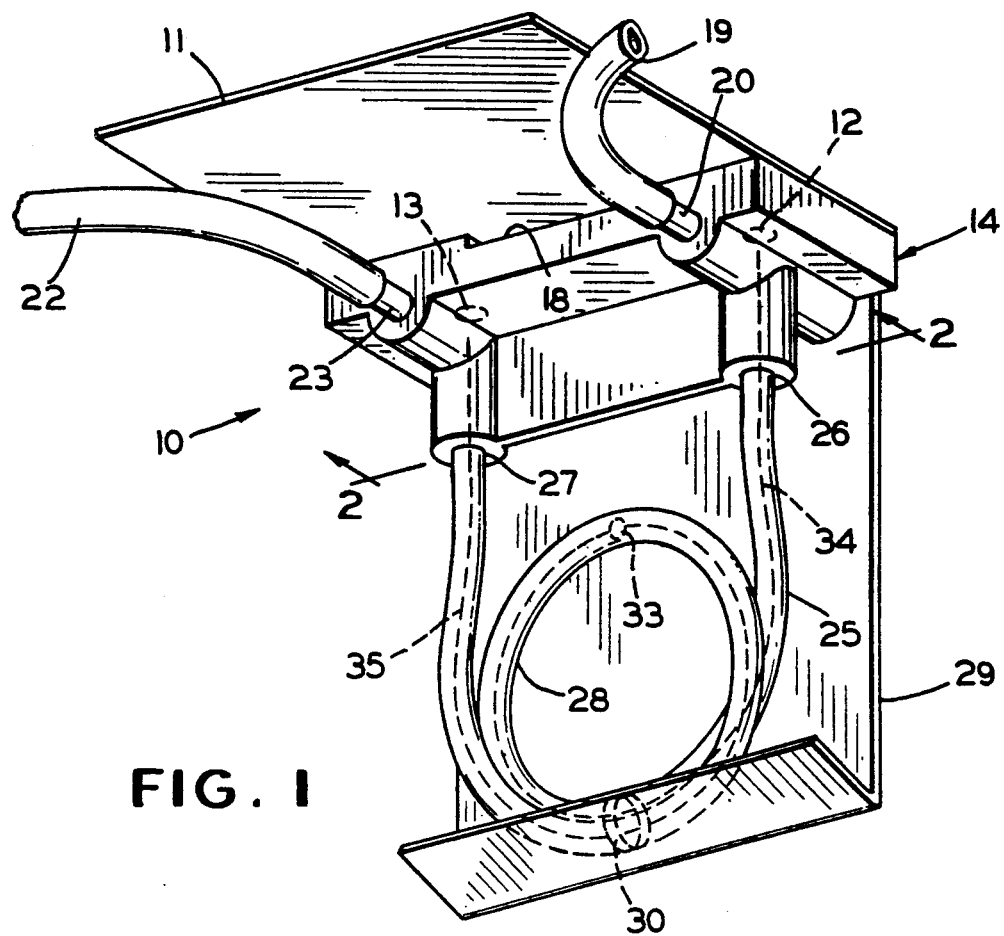
FIG. 1 is a perspective view of sonic cell for a gas concentration and/or bulk gas flow sensor according to the invention.
Figure 2:
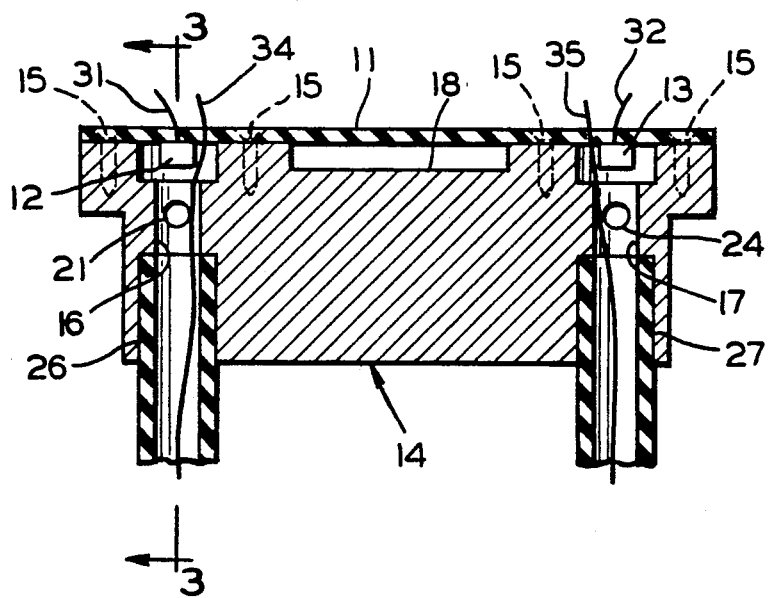
FIG. 2 is a fragmentary cross sectional view as taken along line 2—2 of FIG. 1.
Figure 3:
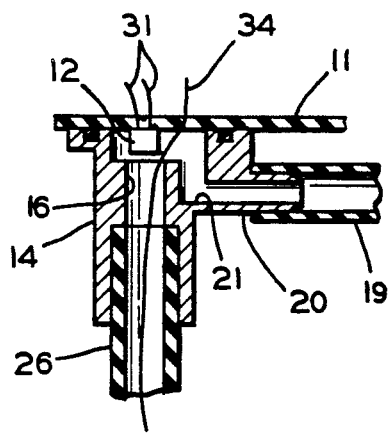
FIG. 3 is a fragmentary cross sectional view as taken along line 3—3 of FIG. 2.

Referring to FIGS. 1-3 of the drawings, a sonic cell 10 is shown for a gas concentration and/or gas bulk flow sensor according to the invention. The sonic cell 10 includes a printed circuit board 11 on which is mounted a portion of the circuitry (not shown) for the sensor. A pair of piezoelectric transducers 12 and 13 are mounted on the printed circuit board 11. The transducers are spaced apart by a predetermined small distance, such as about 2.5 inches (6.35 cm). Mounting the transducers 12 and 13 directly and close together on the printed circuit board 11 provides for manufacturing ease and also minimizes the length of electrical connections between the transducers 12 and 13 and associated circuitry to reduce electrical noise in the circuitry.

A manifold block 14 is secured by a number of screws 15 to the printed circuit board 11 to cover the transducers 12 and 13. The manifold block 14 forms a chamber 16 enclosing the transducer 12 and a chamber 17 enclosing the transducer 13. The chambers 16 and 17 are isolated from one another. A recess 18 is formed in the manifold block 14 adjacent the printed circuit board 11 between the chambers 16 and 17 to permit clearance of circuit board components. A tube 19 is secured to a fitting 20 on the manifold block 14. A passage 21 (FIGS. 2 and 3) through the fitting 20 leads to the chamber 16. Similarly, a tube 22 (FIG. 2) is secured to a fitting 23 on the manifold block 14. A passage 24 through the fitting 23 leads to the chamber 17. An elongated small diameter tube 25 has an end 26 secured to the manifold block 14 to be in communications with the chamber 16 and has an opposite end 27 secured to the manifold block 14 to be in communications with the chamber 17. The manifold block 14 and the tube 25 may be formed from various materials. For example, sonic cells have been successfully constructed with both the manifold block 14 and the tube 25 made from a thermoplastic polyether based polyurethane and they have been made with the manifold block 14 formed from Delrin and the tube 25 formed from polyvinyl chloride (PVC).

The gas under test is delivered to the sonic cell 10 through, for example, the tube 19 to flow sequentially through the chamber 16, the tube 25 and the chamber 17 to the tube 22. Or, the gas may flow in the reverse direction through the sonic cell 10. The gas flow through the sonic cell 10 is directed over both of the transducers 12 and 13. Preferably, the chambers 16 and 17 are designed to direct the air flow around the transducers 12 and 13 with minimum turbulence. In order to reduce the overall dimensions of the sonic cell 10, the tube 25 preferably is wound into a coil 28. By winding the tube 25 into a coil 28, a long tube be provided in a small space. A bracket 29 is shown secured to the manifold block 14 for mounting the sonic cell 10 in application. Also, the coil 28 may be supported by securing it to the bracket 29 with a wire tie 30.

The long flow path provided by the coiled tube 25 provides several other advantages. The long path allows accumulation of significant differences in travel time with or against the gas flow, thereby enabling food resolution of gas flow rate. Further, when the transducers are aligned with a short distance between the transducers, the housing for the transducers must be designed to minimize turbulence which might adversely affect the measured time. Since the travel time for the sonic pulse will be quite short with the transducers closely spaced, the adverse affects of turbulence in the flowing gas will be increased. Complex design considerations were necessary in the past to assure laminar flow at the transducers. With the long flow path provided by the coiled tube 25, the effects of turbulence are averaged out. Measurement over a flow path several wavelength long renders negligible the small impact of pressure on the transducers and reduces the impact of ambient temperature on the receiving transducer's response slope. Finally, the long flow path allows for single point calibration of the sonic cell 10. For long tubes 25, manufacturing variations in tube length lead to variations in the slope term in the formula used to calculate gas concentration which are sufficiently small that they may be ignored and the slope term may be assumed to be constant from sonic cell to sonic cell. This allows for a single point calibration which is faster and easier to evaluate as a quality control parameter.

To minimize attenuation of the sonic wave as it travels through the tube 25, the optimal inside diameter of the tube should be equal to the wavelength of the sonic wave. For example, if the transducers 12 and 13 have a natural frequency of 40 KHz., the tube 25 optimally has an inside diameter of about 7.5 mm or about 0.3 inch. The sonic cell 10 will function with other inside diameters for the tube 25. However, attenuation will increase with larger or smaller diameters. For example, the signal measured at a receiver connected to a transducer at the end of a 13 inch (0.33 meter) tube through which a 40 KHz. ultrasonic wave was transmitted was 3.03 volts for a tube having an inside diameter of 0.375 inch (0.95 cm), was 2.32 volts for a tube having an inside diameter of 0.500 inch (1.27 cm) and was 0.75 volts for a tube having an inside diameter of 0.688 inch (1.75 cm). Similar decreases will be found when the inside diameter is decreased below the optimum diameter. These are several advantages of using transducers 12 and 13 with high resonant frequencies and a small diameter tube 25. The transducers 12 and 13 will have a smaller diameter for higher frequencies. The smaller diameter typically reduces both the cost and power consumption of the transducers. The higher frequency also has less attenuation both for smaller diameter tubes and for smaller coil diameters. Further, it results in more wavelengths for a given coil length, leading to improved accuracy. The small inside diameter of the tube 25 will increase the flow velocity of the gas for a given bulk flow rate, thus producing a higher resolution of the bulk flow rate. Finally, the small inside diameter permits a tighter coil 28, thus reducing the overall size of the sonic cell 10 and it represents a manufacturing cost reduction. The use of the tube 25 assures that the path for the sonic wave will always be greater than the spacing between the transducers 12 and 13. For shorter lengths of the tube 25, the coil 28 may only extend 180°. As the length of the tube 25 increases, the number of windings of the coil 28 may increase.

The length of the coiled tube 25 is selected by balancing two factors. First, the accuracy of the measurements is increased with increased tube length. On the other hand, the amplitude of the signal at the receiving end of the tube falls off as a function of the square root of the tube length. For example, for a tube having an inside diameter of 0.375 inch (0.95 cm) excited with a 40 KHz. ultrasonic wave, a signal of 3.03 volts was observed at a receiver connected to a transducer at the receiving end of a 13 inch (0.33 meter) tube, a signal of 2.27 volts was observed at the receiver for a 21.5 inch (0.55 meter) tube, a signal of 1.45 volts was observed at the receiver for a 32 inch (0.81 meter) tube and a signal of 1.27 volts was observed at the receiver for a 43.5 inch (1.10 meter) tube. A 32 inch (0.81 meter) tube has been found to be a good compromise for a commercial sonic cell.

In operation of the sonic cell 10, preferably a single electric pulse is applied, for example, through wires 31 to the transducer 12. The pulse causes the transducer 12 to move to generate a sonic wave which travels from the chamber 16 through the tube 25 to the chamber 17, where it is received by the transducer 13. In response to sensing the sonic wave, the transducer 13 generates an electric signal which appears on wires 32. Subsequently a single electric pulse is applied through the wires 32 to excite the transducer 13 to transmit a sonic wave which travels through the tube 25 and is received by the transducer 12. As will be explained below, the times that the sonic wave takes to travel in opposite directions between the transducers 12 and 13 are measured and used to calculate the composition of the gas in the tube 25 and/or to calculate the bulk flow rate of the gas through the tube 25.

Although the transducers 12 and 13 may be excited by a burst of ultrasonic waves, it is preferable to use a single short duration pulse to excite the transmitting transducer. By using a single pulse, the noise duration is shortened to a level which can be ignored. A single pulse also reduces power consumption over generating bursts of ultrasonic waves. This in turn reduces heating of the transducers 12 and 13. Minimizing heating of the transducers 12 and 13 diminishes the compensation required for the effect of temperature on the response of the receiver transducer. Optimally, the length of the single pulse is one half wavelength of the natural resonant frequency of the transducers 12 and 13.

The speed at which the sonic wave travels through the gas in the tube 25 will be dependent on the absolute temperature of the gas. A thermistor 33 is located within the tube 25. Preferably, a thermistor 33 having a small bead size is used to provide a fast response time at a high level of resolution and accuracy. The thermistor 33 is generally centered in the coiled tube 25 between the tube ends 26 and 27. One lead 34 from the thermistor 33 extends through the tube 25 to exit the end 26 and to pass through the chamber 16 and the printed circuit board 11. A second lead 35 from the thermistor 33 extends through the tube 25 to exit the end 27 and pass through the chamber 17 and the printed circuit board 11. Locating the thermistor 33 in the center of the tube 25 provides several benefits. External thermal effects are minimized and a more accurate measurement of the average gas temperature over the length of the tube 25 may be made. Further, the thermistor leads 34 and 35 will be exposed to and will be at the gas temperature so that they will aid in bringing the thermistor bead to the gas temperature and will not adversely influence the measured temperature. This arrangement provides a substantially more meaningful measurement of the temperature of the flowing gas than a thermistor which is mounted on and influenced by a surface of the printed circuit board 11 or, in worst cases, which is actually mounted external to the flowing gas stream.

Figure 4:
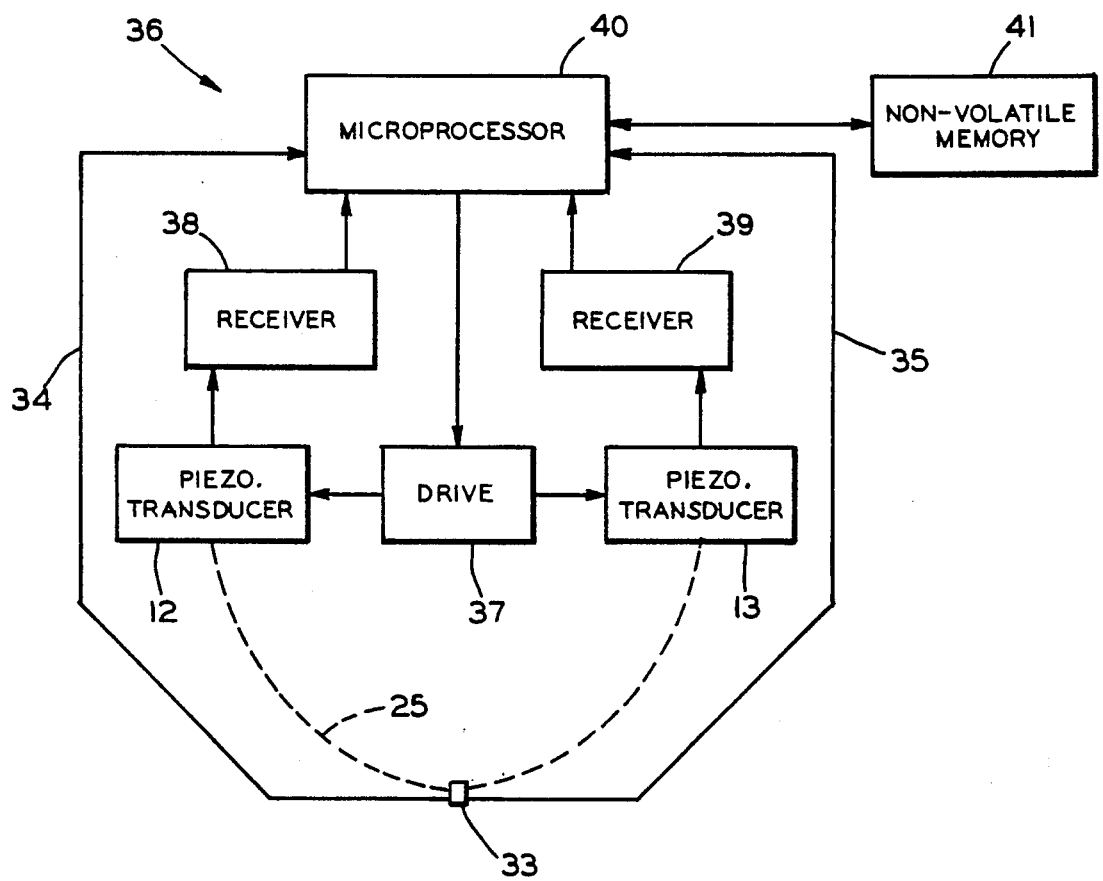
FIG. 4 is a schematic block diagram showing circuitry for operating the sensor of the invention.

FIG. 4 is a block diagram showing circuitry 36 for operating the transducers 12 and 13, for reading the temperature sensed by the thermistor 33 and for calculating a gas concentration or the bulk flow rate of gas flowing through the sonic cell 10. A driver 37 alternately applies an electric pulse to the transducers 12 and 13 to transmit sonic waves through the tube 25 (FIG. 1). The transducer 12 also is connected to a receiver 38 and the transducer 13 also is connected to a receiver 39. The receivers 38 and 39 are amplifiers for the sonic signals received by the transducers 12 and 13, respectively. The driver 37 and the receivers 38 and 39 are connected to a microprocessor 40, which includes a non-volatile memory 41. The memory 41 stores formulas for use by the microprocessor 40 in calculating the percentage of a component of the gas and in calculating the bulk flow rate of the gas. The microprocessor 40 is programmed to cause the driver 37 to alternately apply a short duration single trigger pulse to the transducers 12 and 13. For example, the driver may apply a single 12.5 $\mu$s 24 volt pulse to the transducer 12. When a pulse is applied to the transducer 12, a sonic wave is established in the manifold chamber 16. At the same time, a counter in the microprocessor 40 is enabled to count pulses from a clock. The counter accumulates the pulse count while the sonic wave travels through the tube 25 to the other transducer 13. In response to excitation by the sonic wave, the receiving transducer 13 applies a signal to the receiver 39 which in turn is amplified and applied to the microprocessor 40 to interrupt the clock pulse count. The accumulated clock pulse count is a function of the time taken for the sonic wave to travel between the transducers 12 and 13. For the next period, the transducer 13 is driven as a transmitter to generate a sonic pulse and the transducer 12 is operated as a receiver. Consequently, one time measurement represents the sonic wave travel time in the gas flow direction and the next time measurement represents the sonic wave travel time opposite the gas flow direction.

The microprocessor 40 calculates the concentration of a gas constituent according to the formula:

$$P = C_1 \left(\frac{1}{T}\right)\left(\frac{1}{t_f + t_r}\right)^2 + C_2 T + C_3$$

wherein P is the percentage concentration of the measured gas constituent, $C_1$, $C_2$ and $C_3$ are constants for the sonic cell 10, T is the absolute temperature sensed by the thermistor 33, $t_f$ is the measured time for the sonic wave to travel between the sensors 12 and 13 in the direction of gas flow through the tube 25 and $t_r$ is the measured time for the sonic wave to travel between the sensors 12 and 13 in a direction against the gas flow through the tube 25. The constant $C_1$ is solely a function of the design (primarily path length) of the sensor. $C_1$ can be determined empirically once, with a single sonic cell 10, and then applied equally to all further sonic cells 10 of the same design. The constant $C_2$ is a function of the coil material and the temperature response characteristics of the transducers 12 and 13. When the coil material and transducers are specified, $C_2$ also can be determined empirically by solving simultaneously sets of the above equation for data generated at several temperatures. Determined in this manner, the same value for $C_2$ may be applied to all sensors of the same design. The constant $C_3$ varies from unit to unit and is measured specifically for each sensor by means of calibration with a gas standard of known composition, for example, percentage oxygen. Accordingly, once $C_1$ and $C_2$ are determined for a particular sonic cell design, only a single calibration ($C_3$) is required during production of the sonic cell 10. The constants $C_1$, $C_2$ and $C_3$ are stored in the non-volatile memory 41 along with the above formula for use by the microprocessor 40 in solving the above equation.

The bulk flow rate of the gas may be calculated in liters per minute from the measured forward and reverse times and the formula:

$$V = 2.356 \times 10^4 LD^2 \left( \frac{1}{t_f} - \frac{1}{t_r} \right)$$

wherein V is the bulk gas flow rate through the tube 25, L is the length of the gas flow path between the sensors 12 and 13 through the tube 25 and D is the inside diameter of the coil 28. Various equivalent forms of the above equation are well known and may be found in many texts covering the physics of sound propagation.

In an exemplary sonic cell 10, a tube having a length of 0.8128 meters and a diameter of 0.00798 meters was used. The constants were $C_1 = -6.008$, $C_2 = -0.273$ and $C_3 = 905.3$. The measured temperature T was 298.0° Kelvin, the forward sonic wave travel time was $t_f = 0.002625$ second and $t_r = 0.0026368$ second. Using this data, the bulk flow rate V was calculated as 2.0 liters per minute and the oxygen concentration P was calculated as 95.7%. Other sensors were successfully tried with tubes 25 having lengths ranging form 0.33 meters to 1.09 meters.

It will be appreciated that various modifications and changes may be made to the above described preferred embodiment of a gas concentration and/or flow sensor without departing from the spirit and the scope of the following claims. Although the sensor has been described for measuring both the bulk flow rate of a gas and the concentration of a component of the gas, it will be appreciated that the sensor may be used for measuring only one of these properties when there is no need to measure the other property.

We claim:

1. A sensor for determining at least one of the bulk flow rate of a gaseous medium and the content of a component of the gaseous medium comprising first and second piezoelectric transducers mounted a predetermined distance apart, said transducers having a predetermined high resonant frequency, a tube extending between said transducers, said tube having a first end adjacent said first transducer and a second end adjacent said second transducer, having a length greater than said predetermined distance and having a predetermined small internal diameter, means for flowing a gaseous medium through said tube, means for alternately applying an electric pulse to said first and second transducers, each transducer establishing a wave which travels through the gaseous medium in said tube to the other transducer in response to an applied pulse, means for measuring the time for each such wave to pass between said transducers, means for measuring the temperature of the gaseous medium flowing through said tube, and means responsive to measured times for the wave to travel in the gas flow direction and to travel opposite the gas flow direction and to the measured temperature for determining at least one of the bulk flow rate of the gaseous medium through said tube and the content of a component of the gaseous medium.

2. A sensor, as set forth in claim 1, wherein said means for alternately applying an electric pulse to said first and second transducers applies a single pulse having a length of substantially one half the wavelength of said predetermined high resonant frequency.

3. A sensor, as set forth in claim 1, wherein said temperature measuring means is located in substantially the center of said tube.

4. A sensor, as set forth in claim 3, wherein said temperature measuring means is a thermistor having first and second leads, and wherein said first lead extends from said first tube end and said second lead extends from said second tube end.

5. A sensor, as set forth in claim 1, wherein said determining means is a microprocessor.

6. A sensor, as set forth in claim 5, wherein said means responsive to measured times and to the measured temperature determines the content of a component P of the gaseous medium according to the formula $$P = C_1 \left( \frac{1}{T} \right) \left( \frac{1}{t_f + t_r} \right)^2 + C_2 T + C_3,$$

wherein $C_1$, $C_2$ and $C_3$ are constants, T is the measured absolute temperature of the gaseous medium, $t_f$ is the measured time in the gas flow direction and $t_r$ is the measured time opposite the gas flow direction.

7. A sensor, as set forth in claim 5, wherein said means responsive to measured times and to the measured temperature determines the bulk flow rate of the gaseous medium according to the formula $$V = 2.356 \times 10^4 LD^2 \left( \frac{1}{t_f} - \frac{1}{t_r} \right),$$

wherein L is the length of the flow path between the transducers, D is the inside diameter of the tube, $t_f$ is the measured time in the gas flow direction and $t_r$ is the measured time opposite the gas flow direction.

8. A sensor, as set forth in claim 1, wherein said tube is formed into a coil of at least one loop.

9. A sensor, as set forth in claim 1, wherein said predetermined small internal diameter of said tube is substantially the same as the wavelength of said predetermined high resonant frequency of said transducers.

10. A sensor, as set forth in claim 1, and further including a printed circuit board, wherein said transducers are mounted on said printed circuit board, a manifold forming a first chamber around said first transducer and forming a second chamber around said second transducer, wherein said first tube end communicates with said first chamber and said second tube end communicated with said second chamber, and wherein said means for flowing a gaseous medium through said tube includes means for delivering such gaseous medium to said first chamber and for removing said gaseous medium from said second chamber.

11. A sensor, as set forth in claim 10, wherein such gaseous medium is delivered to said first chamber to flow around said first transducer and such gaseous is caused to flow around said second transducer as it is removed from said second chamber.

12. A sensor, as set forth in claim 11, wherein said manifold and said tube are made of a plastics material.

13. A sensor, as set forth in claim 12, wherein said tube is formed into a coiled loop, and further including a bracket secured to said manifold, and means for supporting said coiled loop from said bracket.

14. A sensor, as set forth in claim 13, and wherein said temperature measuring means comprises a thermistor located in substantially the center of said tube, said thermistor having a first lead which extends from said first tube end and having a second end which extends from said second tube end.

15. A sensor, as set forth in claim 14, and wherein said predetermined small internal diameter of said tube is substantially the same as the wavelength of said predetermined high resonant frequency of said transducers.

* * * * *

REEXAMINATION CERTIFICATE (2633rd)

United States Patent [19]

Frola et al.

[11] B1 5,247,826

[45] Certificate Issued Jul. 18, 1995

[54] GAS CONCENTRATION AND/OR FLOW SENSOR

[75] Inventors: Frank R. Frola, Trafford; Dennis Gibboney, Mt. Pleasant; Paul Bauer, Brentwood, all of Pa.

[73] Assignee: DeVilbiss Health Care, Inc., Somerset, Pa.

Reexamination Request:
No. 90/003,636, Nov. 10, 1994

Reexamination Certificate for:
Patent No.: 5,247,826
Issued: Sep. 28, 1993
Appl. No.: 975,616
Filed: Nov. 12, 1992

[51] Int. Cl.⁶ ............................................. G01N 29/18
[52] U.S. Cl. .................................. 73/24.01; 73/861.28
[58] Field of Search ........................... 73/24.01, 861.28

[56] References Cited

U.S. PATENT DOCUMENTS 4,353,123  10/1982  Rost et al. ........................... 367/137
4,506,453  3/1985  Kamp ................................... 73/61 R

FOREIGN PATENT DOCUMENTS 2211644  7/1974  France .
1228835  11/1966  Germany .

OTHER PUBLICATIONS

Journal of Physics E/Scientific Instruments, vol. 10, No. 12, Dec., 1987, Bristol, Great Britain, pp. 1465–1468, P. Hiismäki and V. Kämäräinen, "A hygrometer based on measuring the speed of sound and the temperature".

*Primary Examiner*—Hezron E. Williams

[57] ABSTRACT

A gas concentration and/or bulk flow rate sensor suitable for measuring the oxygen concentration and the bulk flow rate of gas delivered to a patient for medical purposes. Two piezoelectric transducers mounted on a printed circuit board are interconnected by an elongated coiled tube. The gas is flowed around one of the transducers, through the tube and around the other transducer. Periodically, one of the transducers is energized with a single short duration pulse to transmit a sonic wave through the gas to the other transducer. The travel time for the sonic wave is measured. The two transducers are alternately used as transmitters and receivers so that the wave travel time is measured both with and against the gas flow direction. A thermistor is located in the center of the coiled tube for measuring the temperature of the gas. From the measured times, the measured temperature and stored formulas, a microprocessor calculates the oxygen concentration and/or the bulk flow rate for the gas. The sensor also may be used to measure other components of a gas mixture.

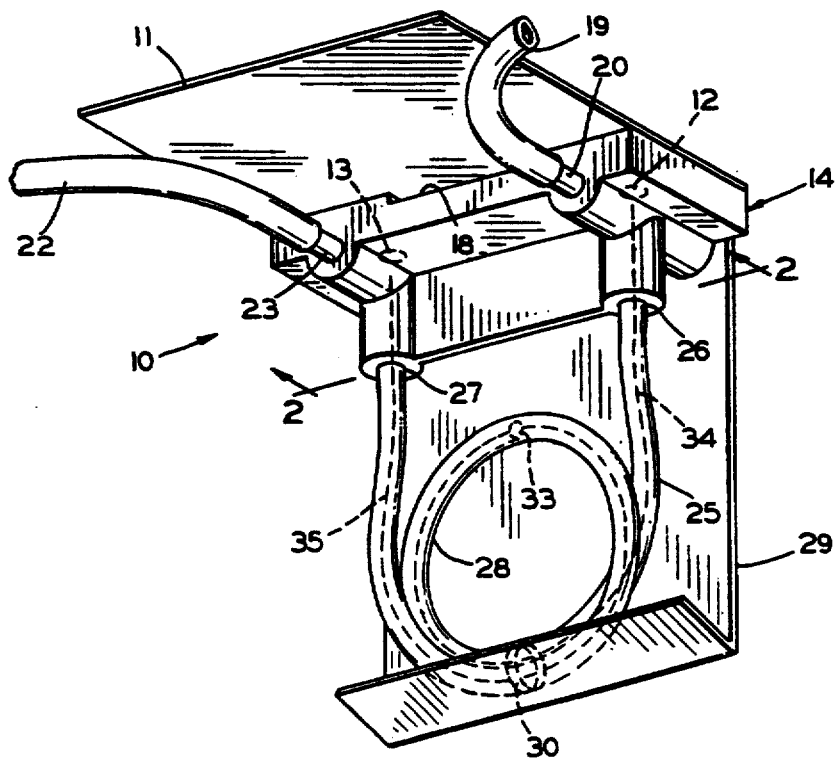

[B1 5,247,826]

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claim 1 is determined to be patentable as amended.

Claims 3–15, dependent on an amended claim, are determined to be patentable.

1. A sensor for determining at least one of the bulk flow rate of a gaseous medium and the content of a component of the gaseous medium comprising first and second piezoelectric transducers mounted a predetermined distance apart, said transducers having a predetermined high resonant frequency, a tube extending between said transucers, said tube having a first end adjacent said first transducer and a second end adjacent said second transducer, having a length greater than said predetermined distance and having a predetermined small internal diameter, means for flowing a gaseous medium through said tube, means for alternately applying an electric pulse *having a length of substantially one half the wavelength of said predetermined high resonant frequency* to said first and second transducers, each transducer establishing a wave which travels through the gaseous medium in said tube to the other transducer in response to an applied pulse, means for measuring the time for each such wave to pass between said transducers, means for measuring the temperature of the gaseous medium flowing through said tube, and means responsive to measured times for the wave to travel in the gas flow direction and to travel opposite the gas flow direction and to the measured temperature for determining at least one of the bulk flow rate of the gaseous medium through said tube and the content of a component of the gaseous medium.

* * * * *